United States Patent [19]
Joslin

[11] Patent Number: 5,394,426
[45] Date of Patent: Feb. 28, 1995

[54] DIODE LASER BAR ASSEMBLY

[75] Inventor: David E. Joslin, Valley Village, Calif.

[73] Assignee: Hughes Aircraft Company, Los Angeles, Calif.

[21] Appl. No.: 976,072

[22] Filed: Nov. 13, 1992

[51] Int. Cl.$^6$ ............................................. H01S 3/19
[52] U.S. Cl. ........................................ 372/50; 372/36
[58] Field of Search .............................. 372/50, 36, 49

[56] References Cited

U.S. PATENT DOCUMENTS

| | | | |
|---|---|---|---|
| 5,084,886 | 1/1992 | Martin | 372/36 |
| 5,099,488 | 3/1992 | Ahrabi et al. | 372/36 |
| 5,325,384 | 6/1994 | Herb et al. | 372/36 |

OTHER PUBLICATIONS

Hutchins, "Magnetic-Self-Alignment of GaAs Laser Arrays to Heat-Sink Arrays" IBM Technical Disclosure Bulletin, vol. 19, No. 4, Sep. 1976, p. 1459.

*Primary Examiner*—Georgia Y. Epps
*Attorney, Agent, or Firm*—Michael W. Sales; Wanda K. Denson-Low

[57] ABSTRACT

Laser apparatus comprising a support that is operative as a heat sink, a diode laser bar assembly, a metallized insulating layer disposed between the substrate and laser bar assembly and an interconnection layer adapted to couple the substrate to the laser bar assembly by means of the metalized insulating layer. The diode laser bar assembly comprises a plurality of laser diode bars having a plurality of lasing sections formed along a lateral edge thereof. First and second metal contacts are disposed on respective adjacent lateral edges of adjacent diode bars, and the metal contacts are separated by a thin layer of metal alloy. One contact forms a positive electrical contact for one laser bar, and the other metal contact forms a negative contact for the adjacent laser bar. A dielectric mirror is disposed on a bottom surface of each of the laser diode bars and an antireflection coating disposed on a top surface of each of the laser diode bars. The present laser apparatus reduces the complexity and cost of diode laser arrays and provides for increased peak power output and improved heat removal. The present diode laser bar assembly may be used in laser surgery systems, solid laser welding, and x-ray photolithography systems where giant pulse solid state lasers are used to create plasmas that generate x-rays. The advantages provided by the diode laser bar assembly are longevity, less heat generation in solid state lasers that are pumped, and greater overall conversion efficiency.

9 Claims, 2 Drawing Sheets

BRICK WORK

BRICK WORK WITH DEAD BAR

LARGE SPACING

DIODE LASER BAR ASSEMBLY

BACKGROUND

The present invention relates generally to diode lasers and more particularly to a diode laser bar assembly that has greater laser bar density and improved heat transfer and efficiency, and increased peak power output.

A "rack and stack" diode laser array configuration is conventionally employed as a diode array structure. In this configuration a laser bar is first mounted on a heat sink. Electrical insulation of individual racks is required. The waste heat generated by the diode laser bar must dissipate through the racks to the reach the heat sink, which requires good thermal contact between the diode laser bar and rack and between the rack and the substrate (heat sink). In the "rack and stack" configuration, individual diode laser bars must first receive optical coatings before being bonded to the rack. Rack fabrication also requires handling individual diode laser bars.

SUMMARY OF THE INVENTION

The present invention provides for laser apparatus comprising a support that is operative as a heat sink to cool a diode laser bar assembly, a metallized insulating layer disposed between the heat sink and laser bar assembly and an interconnecting layer adapted to couple the heat sink to the laser bar assembly. The diode laser bar assembly comprises a plurality of laser diode bars having a plurality of lasing sections formed along a lateral edge thereof. First and second metal contacts are disposed on respective adjacent lateral edges of adjacent diode bars, and the metal contacts are separated by a thin layer of metal alloy. One contact forms a positive electrical contact for one laser bar, and the other metal contact forms a negative contact for the adjacent laser bar. A dielectric mirror is disposed on a bottom surface of each of the laser dime bars and an antireflection coating disposed on a top surface of each of the laser diode bars.

The layer of insulating material is disposed adjacent the bottom surfaces of the laser bars, the first and second metal contacts and layer of metal alloy. The metallization layer is disposed on the layer of insulating material. The interconnection layer is disposed between the metallization layer and the substrate and is adapted to secure the diode laser bar assembly to the substrate.

The present invention thus provides for a laser structure that reduces the complexity and cost of diode laser arrays and provides for increased peak power output and improved heat removal. The improvements provided by the present diode laser array of the present invention are achieved by the thin electrically insulating polyimide film underneath the array of diode laser bars. The individual diode laser bars are bonded together in series to form a unit or subassembly before application of optical coatings and the (polyimide) insulating film. The exposed insulating film is metalized to allow for indium solder bonding of the diode laser bar assembly to a heat sink such as a micro-channel cooler.

By first bonding the bars together in a subassembly, handling of individual bars is obviated during subsequent operations. Because the intermediate substrate (rack) found in current designs is eliminated, the initial number of parts required in the diode laser array is roughly halved. Further, by eliminating the rack, a greater bar density is achieved, permitting up to 45 bars per centimeter. Uniform diode laser bar assembly performance is provided by the present invention, and is a function of uniformly grown crystals available using large area MOCVD reactors. When the diode laser bar assembly is bonded to the heat sink, the peak power output of the array may be greater than or equal to 2,000 Watts per square centimeter. To compensate for this, the lasing sections along the dime laser bar may be staggered to improve lateral heat dissipation. Since a primary application for these arrays is pumping solid state lasers, the increased energy density provided by the present invention allows for more compact optical coupling between a dime laser bar assembly and the solid state laser.

The present dime laser assembly may be used as a replacement of flash lamps in laser surgery systems, solid laser welding, and in x-ray photolithography systems where giant pulse solid state lasers are used to create plasmas that generate x-rays. The advantages provided by the diode laser apparatus of the present invention over flash lamp systems include longevity, less heat generation in the solid state laser rod, and greater overall conversion efficiency.

BRIEF DESCRIPTION OF THE DRAWINGS

The various features and advantages of the present invention may be more readily understood with reference to the following detailed description taken in conjunction with the accompanying drawings, wherein like reference numerals designate like structural elements and in which.

DETAILED DESCRIPTION

Figure 1:
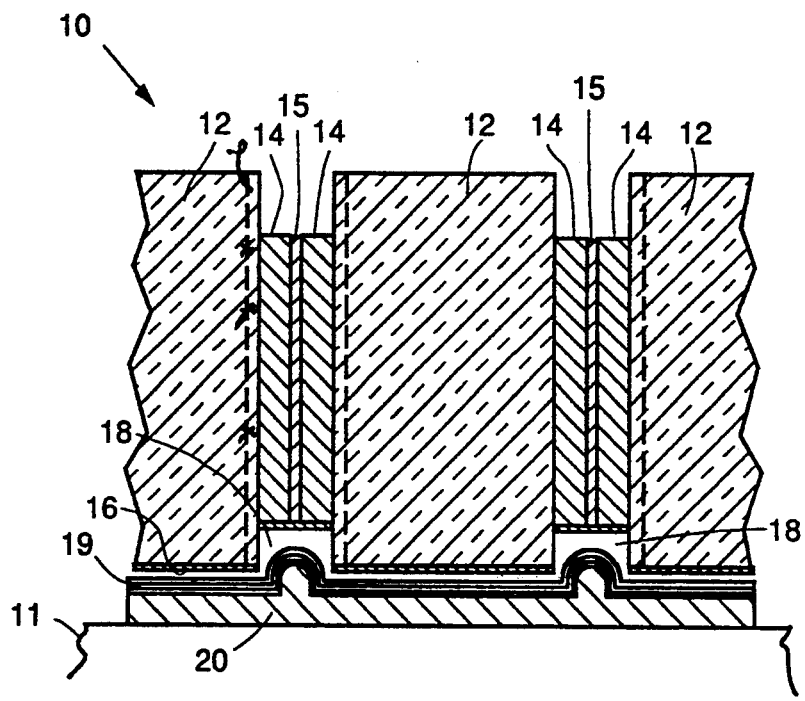
FIG. 1 shows a cross section of a diode laser bar assembly in accordance with the principles of the present invention.
Figure 2:
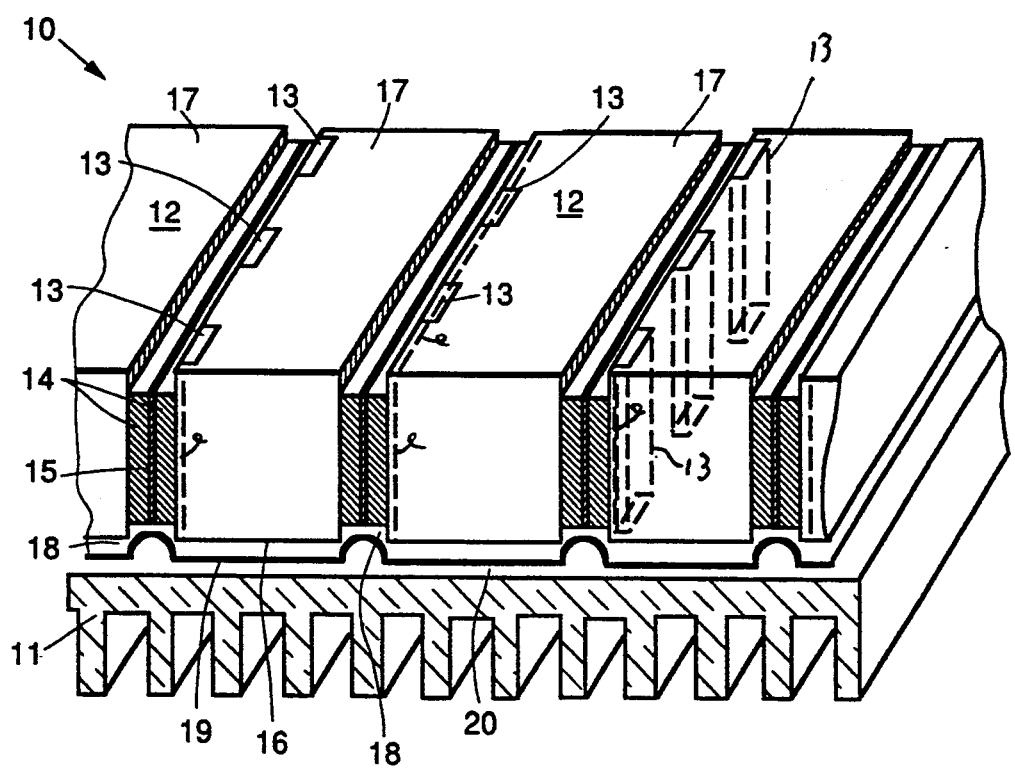
FIG. 2 shows a perspective cross sectional view of the diode laser bar assembly of FIG. 1.

Referring to the drawing figures, FIG. 1 shows a cross section of a diode laser bar assembly 10 in accordance with the principles of the present invention, while FIG. 2 shows a perspective cross sectional view of the diode laser bar assembly 10 of FIG. 1. The diode laser bar assembly 10 is comprised of a silicon substrate, which may comprise a supporting heat sink 11, such as a silicon micro-channel cooler, for example. A plurality of gallium arsenide (GaAs) substrate sections 12 or laser diode bars 12 are provided that typically have dimensions on the order of from 200 to 300 microns in width, 200 to 300 microns in height and 1 centimeter in length. Along the lateral edges of the laser diode bars 12 are formed a plurality of lasing sections 13. Each lasing section 13 is formed in turn by approximately ten closely packed stripe laser. The lasing section 13 along the lateral edge of the bar 12 may occupy 20 percent or greater of the length of the bar 12. The plurality of laser diode bars 12 are disposed adjacent each other to form a diode array and are separated by two metal (silver) contacts 14 that are from 4 to 10 microns in thickness and that are separated by a thin layer of silver alloy 15. One contact 14 is a positive electrical contact for one laser bar 12, while the other metal contact 14 is a negative contact for the adjacent laser bar 12. The silver alloy 15 should have a melting point of about 220° C. to 310° C., which is a function of semiconductor processing temperatures used in processes that fabricate the assembly 10. The metal contacts 14 and layer of alloy 15 are recessed about 5 microns from an edge of the top and bottom edges of the laser diode bars 12.

Figure 3A:
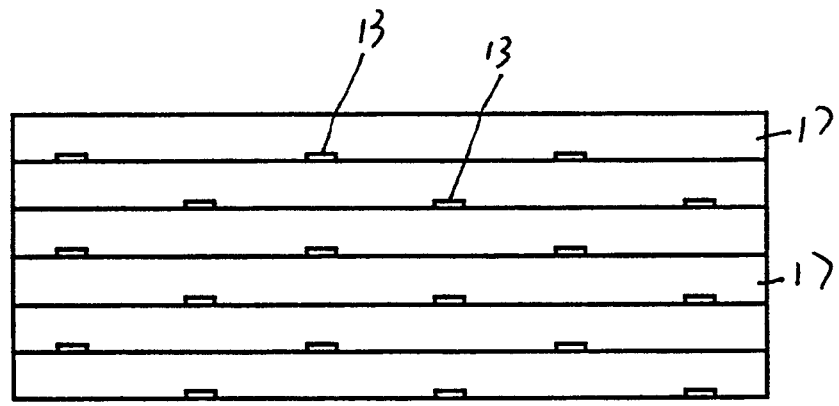
FIGS. 3a–3c illustrate location patterns of lasing sections that may be employed in the diode laser bar assembly of FIGS. 1 and 2.
Figure 3B:
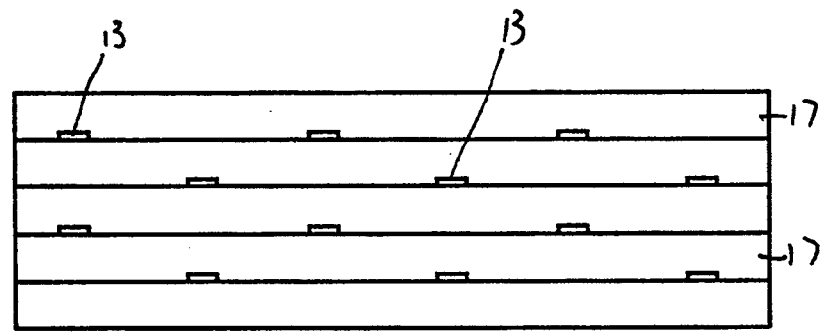
Figure 3C:
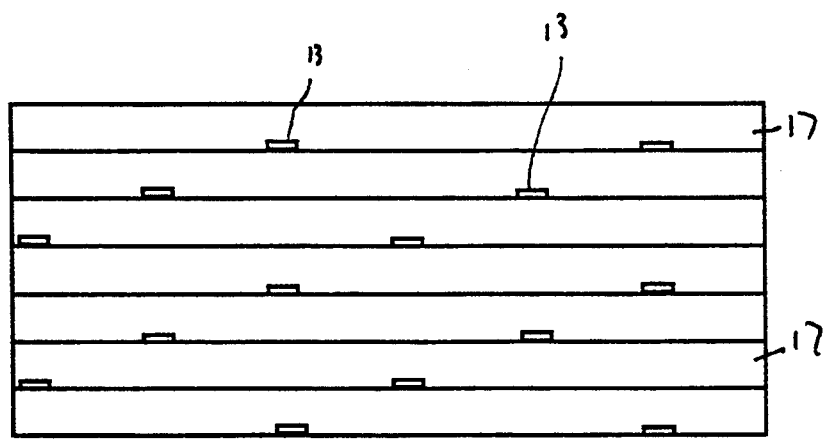

A dielectric mirror 16 is disposed on the bottom surface of each of the laser diode bars 12, and an antireflection coating 17 is disposed on the top surface of each of the laser diode bars 12. The plurality of lasing sections 13 are generally disposed along only one lateral edge of each of the laser diode bars 12. The lasing sections 13 in adjacent laser diode bars 12 are also staggered relative to each other. Several staggering patterns may be employed and FIGS. 3a–3c illustrate location patterns of lasing sections 13 that may be used in the diode laser bar assembly 10 of FIGS. 1 and 2. FIG. 3a illustrates a "brick" or interleaved pattern, FIG. 3b shows an interleaved pattern with unused "dead" diode laser bars 12, and FIG. 3c shows relatively large spacing of the lasing sections 13. The above-described assembly 10 thus forms a subassembly that comprises the stacked diode laser bars 12 interconnected by means of the metal contacts 14 and the layer of alloy 15, and including the antireflection coatings 17 and dielectric mirrors 16.

Adjacent the bottom surface of each of the laser diode bars 12, the metal contacts 14, and layer of alloy 15, is disposed a layer of insulating material 18. The layer of insulating material 18 may be formed from polyimide, for example, and has a thickness of about 1 to 1.5 microns, for example. The surface of the layer of insulating material 18 distal from the diode laser bars 12 is metallized using a relatively thin layer of silver, for example, to form a metallization layer 19. The metallization layer 19 has a thickness of about 2 microns, for example. An interconnection layer 20, comprising a layer of indium solder, for example, is disposed between the metallization layer 19 and the heat sink 11, that is used to secure the diode laser bar assembly 10 to the heat sink 11.

The present invention provides for a laser structure that reduces the complexity and cost of diode laser arrays, and provides for increased peak power output and improved heat removal. The diode laser bar assembly 10 of the present invention disposes the thin electrically insulating polyimide film insulating layer 18 underneath the diode laser bars 12. The individual diode laser bars 12 are bonded together in series to form a unit or subassembly before application of optical coatings 16, 17 and the polyimide film insulating layer 18. The exposed polyimide film insulating layer 18 is metalized (layer 19) to allow for indium solder bonding of the diode laser bar assembly 10 to the heat sink 11.

By first bonding the diode laser bars 12 together into a subassembly, handling of individual bars 12 is obviated during subsequent operations. Because the intermediate substrate (rack) found in current designs is eliminated, the initial number of parts required in the present diode laser bar assembly 10 is roughly halved. Further, by eliminating the rack, a greater bar density is achieved, permitting up to 45 bars 12 per centimeter. Uniform performance of the diode laser bar assembly 10 is provided, based on uniform crystal growth available using large area metal oxide chemical vapor deposition (MOCVD) reactors. When the diode laser bar assembly 10 is bonded to the heat sink 11 comprising the support, the peak power output of the array may increase to over 2,000 Watts per square centimeter. The lasing sections 13 along the diode laser bar 12 are therefore staggered to improve lateral heat dissipation as is shown in FIGS. 3a–3c. Since a primary application for the laser diode bar assembly 10 is in pumping solid state lasers, an increase in energy density may allow for more compact optical coupling between a diode laser bar assembly 10 and the solid state laser.

The diode laser bar assembly 10 is fabricated by first cleaving individual lasing bars 12 that are 1 cm long and 300 microns wide from a 200 micron thick GaAs wafer having the required crystal layers that permit lasing, and then bonding the individual bars 12 together prior to further processing. Typically, the epitaxial crystal layers form a dual heterostructure of an optically confining region surrounding a single quantum well electrically active region. This is generally known and reference is made to a paper entitled "Separate Confinement Heterostructure Single Quantum Well Laser Bar", by M. Sakamoto et al., *Appl. Phys. Lett.*, Vol. 54, page 2299, (1989), which describes such structures. The uniformity of layer thickness and doping available in presently available MOCVD deposition processes produces very narrow lasing line widths of 2.5 nm. The electrical contacts 14 that are disposed over the entire length of each narrow lasing bar 12 are defined by vacuum deposition of metal through a photoresist mask applied to both sides of the wafer. The thickness of the contacts 14 may be increased by plating after the photoresist is removed. Parallel mirror facets created by cleaving the GaAs wafer on its {110} crystal plane, define the ends of a Fabry Perot etalon (300 microns long) that supports oscillation in a GaAs lasing medium comprising the GaAs substrate sections 12.

Each lasing bar 12 has many uniformly spaced lasing sections 13 that occupy between 20% and 30% of its length. The width of the individual lasing section 13 is typically 100 microns with each section 13 comprised of 10 lasing stripes, each 6 microns wide. When the lasing bars 12 are turned on edge and stacked one next to the other for series electrical connection, the light emitting facets for each lasing section 13 face outward as is shown in FIG. 2. The lasing sections 13 are arranged in one of the patterns shown in FIG. 3 from bar 12 to bar 12 to allow maximum separation between each lasing section 13, and so permit uniform heat generation and thermally induced stress over the diode laser bar assembly 10. The bars 12 are stacked with their positive contacts 14 facing the negative contacts 14 of adjacent bars 12.

The optical coatings 16, 17 are applied to the diode laser bar assembly 10 by vacuum deposition. The optical character of the polyimide insulating layer 18 is taken into account as part of the design of the dielectric mirror 16.

The thickness of the polyimide film insulating layer 18 is between 1 and 1.5 microns to withstand a bias condition several times that required for lasing of 45 bars 12 in series. A 1 micron polyimide insulating layer 18 is able to withstand at least 300 volts. However, the polyimide insulating layer 18 is kept intentionally thin to assure low thermal resistance across the polyimide film insulating layer 18. The polyimide insulating layer 17 should have a thermal resistance of about 0.030 C-cm$^2$/W which is comparable to the thermal resistance of the silicon micro-channel heat sink 11.

To better understand the maximum light power and the maximum duty cycle capabilities of the diode laser bar assembly 10, which depend on lasing efficiency and heat dissipation, the temperature rise needs to be simulated over a range of design variables. The most important of these variables include the thickness of the diode laser heat sink 11, the thickness of the silver contacts 14, the thickness of the polyimide film insulating layer 18, the number of lasing sections 13 per length of the bar 12, and the pattern of the lasing sections 13 in the array.

The diode laser bar assembly 10 is operated in pulse mode with a duty cycle of about 2% to 4%. With a controlled temperature rise the peak power available from the diode laser bar assembly 10 could surpass that of the conventional rack and stack configuration. More particularly, the diode laser bar assembly 10 may have between 35 and 45 bars, 12 per centimeter, in the stacked direction which is higher than the standard rack and stack configurations currently available. At 45 bars, 12 per centimeter, the thickness of the bar 12 including contacts 14 is approximately 225 microns. With a nominal light output of 50 Watts peak power per bar 12, the diode laser bar assembly 10 peak power could exceed 2,000 Watts per square centimeter.

The present invention provides protection from the maximum quasi CW power dissipation of the diode laser bar assembly 10 and heat sink 11. The three dimensional nature of the heat flow away from the lasing sections 13 requires the heat to spread laterally through the GaAs substrate sections 12 and the silver electrical contacts 14 before it passes through the polyimide film insulating layer 18 into the heat sink 11.

The assembly process for the diode laser bar assembly 10 is detailed below. The bulk of the metallization for the electrical contacts 14 on either side of the bars 12 is a heavy 4 to 10 micron layer of silver terminating in a silver alloy, having a melting point greater than 220° C. The other component of the alloy, such as tin (Sn), lead (Pb) or indium (In) can be either vacuum-deposited or plated on the surface. Sintering of this structure in an inert atmosphere may be used for dissolution of enough silver to produce a eutectic having the required melting temperature. The wafer is then cleaved to form the single bars 12 approximately 1 cm long. As noted above the width of the bar 12 resulting from the cleaving process defines the length of the optical cavity, approximately 300 microns, and the {011} GaAs facets that form the Fabry Perot etalon.

The bars 12 are stacked together on the heat sink 11 with the lasing facets facing up and the contacts touching. The temperature is then raised above the eutectic melting point. Just enough pressure is applied to allow the molten alloy to bridge the space between the electrical contacts 14 but not enough pressure to squeeze the alloy from between the bars 12. As the temperature is decreased the point of solidification is verified to meet a minimum of 220° C. This process may require heating the bars 12 in an inert atmosphere or under a partial vacuum to avoid contamination or oxidation of the heat sink 11 or the silver alloy. A minimum eutectic temperature of 220° C. is important because of exposure to a 200° C. temperature required in a later processing step.

After the bars 12 are bonded they may be handled as a unit for subsequent processing. The exposed facets of the diode laser bar assembly 10 then receive the dielectric antireflection and mirror coatings 16, 17. The polyimide film insulating layer 18 is spun on the mirrored bottom surface and cured at minimum temperature of 200° C. to densify it. The last major processing step needed to complete the diode laser bar assembly 10 requires metallization of the polyimide film insulating layer 18 so that it may be soldered to the heat sink 11.

The integration of diode laser pump arrays into solid state laser subsystems to replace conventional flash lamps depends on the cost, ruggedness and ability to cool the diode laser pump arrays. Three advantages are provided by the diode laser pump array (diode laser bar assembly 10) of the present invention over flash lamps. These are longevity, less heat generation in the solid state laser rod, and greater overall conversion efficiency. The present diode laser bar assembly 10 may be used as a replacement of flash lamps in laser surgery systems, some forms of solid laser welding, and in x-ray photolithography systems where giant pulse solid state lasers are used to create plasmas that generate x-rays.

Thus there has been described a new and improved diode laser bar assembly that has greater laser bar density and improved heat transfer and efficiency, and increased peak power output. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. A laser apparatus comprising:
   a substrate comprising a heat sink;
   a diode laser bar assembly comprising:
      a plurality of laser diode bars having a plurality of lasing sections formed along a lateral edge thereof;
      first and second metal contacts disposed on respective adjacent lateral edges of adjacent diode bars, which metal contacts are separated by a thin layer of metal alloy, and wherein one contact forms a positive electrical contact for one laser bar, and the other metal contact forms a negative contact for the adjacent laser bar;
      a dielectric mirror disposed on a bottom surface of each of the laser diode bars; and
      an antireflection coating disposed on a top surface of each of the laser diode bars;
   a layer of insulating material disposed adjacent the bottom surfaces of the laser bars and the first and second metal contacts and layer of metal alloy;
   a metallization layer disposed on the layer of insulating material; and
   an interconnection layer 20 disposed between the metallization layer and the substrate that is adapted to secure the diode laser bar assembly to the substrate.

2. The laser apparatus of claim 1 wherein each of the plurality of laser diode bars comprise gallium arsenide (GaAs) substrate sections.

3. The laser apparatus of claim 1 wherein the first and second metal contacts comprise silver contacts.

4. The laser apparatus of claim 1 wherein the silver alloy has a melting point of between 220° C. and 310° C.

5. The laser apparatus of claim 1 wherein the metal contacts and layer of alloy are recessed from top and bottom edges of the laser diode bars.

6. The laser apparatus of claim 1 wherein each of the plurality of laser diode bars comprise lasing sections that are staggered relative to lasing sections in adjacent laser diode bars.

7. The laser apparatus of claim 1 wherein the layer of insulating material comprises polyimide material.

8. The laser apparatus of claim 1 wherein the metallization layer is applied to the insulating and comprises a relatively thin layer of silver.

9. The laser apparatus of claim 1 wherein the interconnection layer comprises a layer of indium solder.

* * * * *